(12) United States Patent
Hirokami

(10) Patent No.: US 9,464,100 B2
(45) Date of Patent: Oct. 11, 2016

(54) ORGANOSILICON COMPOUND, ADHESIVE COMPOSITION AND ARTICLE

(71) Applicant: Shin-Etsu Chemical Co., Ltd., Tokyo (JP)

(72) Inventor: Munenao Hirokami, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/921,268

(22) Filed: Oct. 23, 2015

(65) Prior Publication Data

US 2016/0039849 A1  Feb. 11, 2016

Related U.S. Application Data

(62) Division of application No. 14/632,182, filed on Feb. 26, 2015.

(30) Foreign Application Priority Data

Mar. 25, 2014 (JP) ................. 2014-061196

(51) Int. Cl.
*C07F 7/18* (2006.01)
*C09D 5/00* (2006.01)
*C09J 11/06* (2006.01)

(52) U.S. Cl.
CPC .......... *C07F 7/1804* (2013.01); *C07F 7/1836* (2013.01); *C09D 5/002* (2013.01); *C09J 11/06* (2013.01)

(58) Field of Classification Search
USPC ................. 556/437, 438, 457, 461
See application file for complete search history.

(56) References Cited

U.S. PATENT DOCUMENTS

2011/0288252 A1* 11/2011 Ballweg ................ C07F 7/184
526/238.1

FOREIGN PATENT DOCUMENTS

| JP | 6-345847 A | 12/1994 |
| JP | 2009-84318 A | 4/2009 |
| JP | 2010-144148 A | 7/2010 |
| WO | WO 2010/055154 A1 | 5/2010 |

OTHER PUBLICATIONS

Aviram, A., "Preparation of Monomolecular Layers of Hemiquinones for Electric Field Switching," Database Caplus [Online] Chemical Abstracts Service, Accession No. 1989:407003, published first Journal of Molecular Electronics, 1988, 1 page, XP-002742229.

Dabaghi et al., "Electrochemical Preparation of New Organosilicone Compounds for Functionalizing of Mesoporous Silica," Database Caplus [Online] Chemical Abstracts Service, Accession No. 2013:901060, published first Functional Materials Letters, 2013, 2 pages, XP-002742228.

Extended European Search Report, dated Jul. 24, 2015, for European Application No. 15155933.3.

Heo et al., "Improved Performance of Protected Catecholic Polysiloxanes for Bioinspired Wet Adhesion to Surface Oxides", Journal of the American Chemical Society, 2012, vol. 134, pp. 20139-20145.

Mizutani et al., "Positive-working Photoresist Composition Containing Specific Polysiloxane for Upper Resist Layer of Composite Two-Layer Resist Structure," Database Caplus [Online] Chemical Abstracts Service, Accession No. 2001:261350, 2001, 4 pages, XP-002742231.

Tanaka et al., "Hydrophilic Hydrolyzable Silyl-Containing Polymer Sol-Gel Compositions with Good Transparency and Friction and Scratch Resistance and Hydrophilic . . . Them," Database Caplus [Online] Chemical Abstracts Service, Accession No. 2009-490316, 2009, 5 pages, XP-002742230.

\* cited by examiner

*Primary Examiner* — Pancham Bakshi

(74) *Attorney, Agent, or Firm* — Birch, Stewart, Kolasch & Birch, LLP

(57) ABSTRACT

An organosilicon compound having a hydrolyzable silyl group and a catechol group in the molecule is novel. When modified by surface treatment with an adhesive composition comprising the organosilicon compound, various inorganic materials such as glass and metals become tightly adherent to epoxy and other resins.

8 Claims, No Drawings

ORGANOSILICON COMPOUND, ADHESIVE COMPOSITION AND ARTICLE

CROSS-REFERENCE TO RELATED APPLICATIONS

This application is a Divisional of co-pending application Ser. No. 14/632,182 filed on Feb. 26, 2015, which claims priority under 35 U.S.C. §119(a) to Patent Application No. 2014-061196 filed in Japan on Mar. 25, 2014. All of the above applications are hereby expressly incorporated by reference into the present application.

TECHNICAL FIELD

This invention relates to an organosilicon compound having a hydrolyzable silyl group and a catechol structure in the molecule, an adhesive composition comprising the compound, and an article comprising a substrate treated with the composition.

BACKGROUND ART

The adhesive protein produced by Mytilus galloprovincialis is a superb underwater adhesive. Recent studies are made on the special chemical structure of this adhesive protein and an adhesion mechanism taking advantage of the chemical structure. Although there is still much to understand about the adhesion mechanism, it is known that a catechol structure compound in the adhesive plays an important role.

Patent Document 1 describes to form a polydopamine thin film to improve the adhesion between a plated leadframe and an epoxy resin or silicone resin. Non-Patent Document 1 discloses the synthesis of a silyl-protected catechol-containing silicone by thiol-ene reaction between a silyl-protected vinyl-containing catechol compound and a mercapto-containing silicone and its use in an adhesive composition.

In some examples, as described above, catechol structure compounds are used as an ingredient for adhesive compositions. However, there are known no reports referring to an organosilicon compound having a hydrolyzable silyl group and a catechol group in the molecule and an adhesive composition containing the same.

CITATION LIST

Patent Document 1: JP-A 2010-144148
Non-patent Document 1: J. Am. Chem. Soc. 2012, 134, 20139-20145

DISCLOSURE OF INVENTION

An object of the invention is to provide an organosilicon compound having a hydrolyzable silyl group and a catechol group in the molecule, an adhesive composition comprising the compound, and an article comprising a substrate treated with the composition.

In one aspect, the invention provides an organosilicon compound of formula (1):

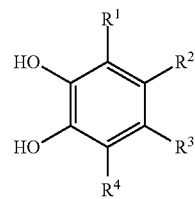

wherein $R^1$ to $R^4$ are each independently selected from the group consisting of hydrogen, substituted or unsubstituted monovalent hydrocarbon groups which may be separated by at least one bond selected from ether, thioether, carbonyl, and thiocarbonyl bonds, and organic groups of formulae (2) to (5), and at least one of $R^1$ to $R^4$ is any one of organic groups of formulae (2) to (5):

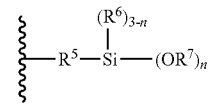

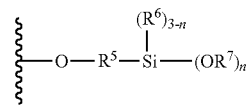

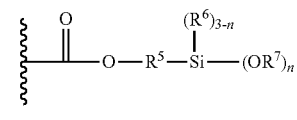

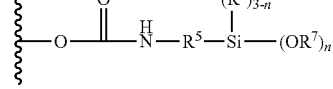

wherein $R^5$ is a substituted or unsubstituted divalent hydrocarbon group which may be separated by at least one bond selected from ether, thioether, carbonyl, thiocarbonyl, amino, urethane, and urea bonds, $R^6$ is an alkyl group of 1 to 10 carbon atoms or aryl group of 6 to 10 carbon atoms, $R^7$ is an alkyl group of 1 to 20 carbon atoms, alkenyl group of 2 to 10 carbon atoms, aryl group of 6 to 10 carbon atoms or acyl group of 1 to 20 carbon atoms, n is an integer of 1 to 3, and the wavy line designates a bonding site to the benzene ring.

In one preferred embodiment, formula (2) is any one of formulae (6) to (10):

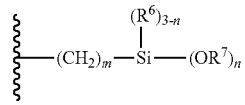

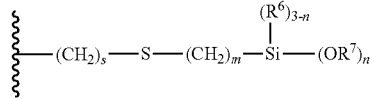

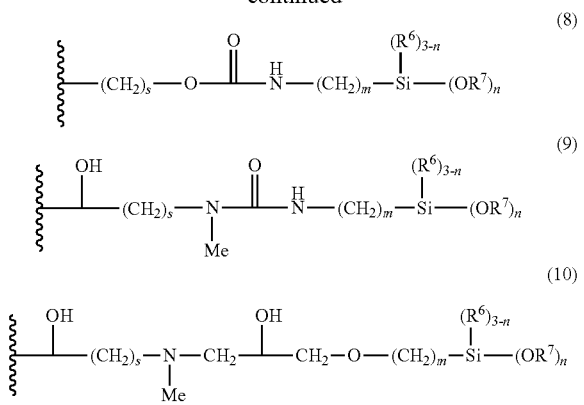

(8)

(9)

(10)

wherein m is an integer of 1 to 8, s is an integer of 1 to 8, $R^6$, $R^7$, n and the wavy line are as defined above, and Me is methyl.

In one preferred embodiment, formula (3) is formula (11) or (12):

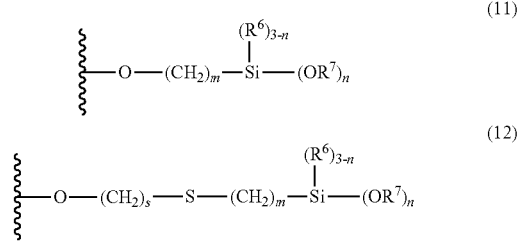

(11)

(12)

wherein $R^6$, $R^7$, n, m, s and the wavy line are as defined above.

In one preferred embodiment, formula (4) is formula (13) or (14):

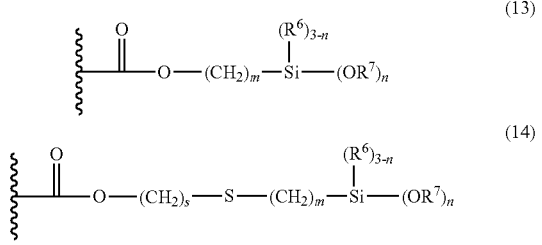

(13)

(14)

wherein $R^6$, $R^7$, n, m, s and the wavy line are as defined above.

In one preferred embodiment, formula (5) is formula (15):

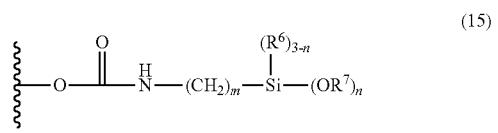

(15)

wherein $R^6$, $R^7$, n, m and the wavy line are as defined above.

In another aspect, the invention provides an adhesive composition comprising the organosilicon compound defined above.

In a further aspect, the invention provides an article comprising a substrate having a surface treated with the adhesive composition defined above. The substrate is typically a glass fiber product selected from among glass cloth, glass tape, glass mat, and glass paper; an inorganic filler; or a ceramic or metal substrate.

Advantageous Effects of Invention

The organosilicon compound of the invention has both a hydrolyzable silyl group and a catechol group in the molecule. When modified by surface treatment with an adhesive composition comprising the organosilicon compound, various inorganic materials such as glass and metals become tightly adherent to resins.

DESCRIPTION OF PREFERRED EMBODIMENTS

As used herein, the term "silane coupling agent" is encompassed by "organosilicon compound".

Organosilicon Compound

The organosilicon compound or silane coupling agent of the invention is characterized by having both structures (i) and (ii):
(i) hydrolyzable silyl group and
(ii) catechol group.

A series of compounds having both structures (i) and (ii) are represented by organosilicon compounds of the following formula (1).

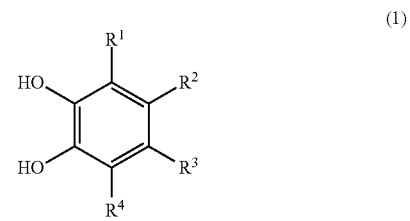

(1)

Herein $R^1$ to $R^4$ are each independently selected from hydrogen, optionally substituted monovalent hydrocarbon groups which may be separated by at least one bond selected from ether, thioether, carbonyl, and thiocarbonyl bonds, and organic groups of formulae (2) to (5). At least one of $R^1$ to $R^4$ must be an organic group selected from formulae (2) to (5).

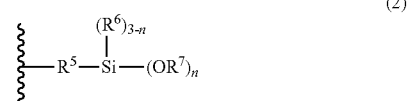

(2)

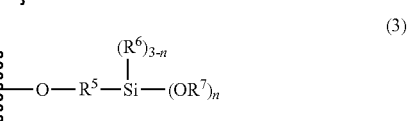

(3)

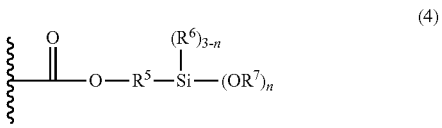

(4)

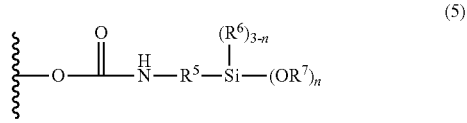

(5)

Herein $R^5$ is an optionally substituted divalent hydrocarbon group which may be separated by at least one bond selected from ether, thioether, carbonyl, thiocarbonyl, amino, urethane, and urea bonds, $R^6$ is an alkyl group of 1 to 10 carbon atoms or aryl group of 6 to 10 carbon atoms, $R^7$ is an alkyl group of 1 to 20 carbon atoms, alkenyl group of 2 to 10 carbon atoms, aryl group of 6 to 10 carbon atoms or acyl group of 1 to 20 carbon atoms, n is an integer of 1 to 3, and the wavy line designates a bonding site to the benzene ring.

When $R^1$ to $R^4$ are independently an optionally substituted monovalent hydrocarbon group of 1 to 10 carbon atoms, preferably 1 to 6 carbon atoms which may be separated by at least one bond selected from ether, thioether, carbonyl, and thiocarbonyl bonds, examples of the monovalent hydrocarbon group include alkyl groups such as methyl, ethyl, propyl, isopropyl, butyl, isobutyl, tert-butyl, pentyl, neopentyl, hexyl and octyl, cycloalkyl groups such as cyclohexyl, alkenyl groups such as vinyl, allyl and propenyl, aryl groups such as phenyl, tolyl, xylyl and naphthyl, and aralkyl groups such as benzyl, phenylethyl and phenylpropyl. Each group of $R^1$ to $R^4$ may have a substituent such as epoxy, acrylic, methacrylic, alcohol (OH), mercapto or amino radical. An ether, thioether, carbonyl or thiocarbonyl bond may intervene in the group as described above.

$R^5$ is an optionally substituted divalent hydrocarbon group of 1 to 10 carbon atoms, specifically 1 to 8 carbon atoms, examples of which include alkylene groups such as methylene, ethylene, propylene, isopropylene, butylene, isobutylene, tert-butylene, pentylene, neopentylene, hexylene and octylene, cycloalkylene groups such as cyclohexylene, alkenylene groups such as vinylene, allylene and propenylene, arylene groups such as phenylene, tolylene, xylylene and naphthylene, and aralkylene groups such as benzylene, phenylethylene and phenylpropylene. When $R^5$ is a substituted group, hydroxyl is a typical substituent. Also at least one bond selected from ether, thioether, carbonyl, thiocarbonyl, amino (—NR— wherein R is H, $C_1$-$C_3$ alkyl or phenyl), urethane, and urea bonds may intervene in the group $R^5$.

$R^6$ is a monovalent hydrocarbon group of 1 to 10 carbon atoms, preferably 1 to 6 carbon atoms, examples of which include alkyl groups such as methyl, ethyl, propyl, isopropyl, butyl, isobutyl, tert-butyl, pentyl, neopentyl, hexyl and octyl, cycloalkyl groups such as cyclohexyl, alkenyl groups such as vinyl, allyl and propenyl, aryl groups such as phenyl, tolyl, xylyl and naphthyl, and aralkyl groups such as benzyl, phenylethyl and phenylpropyl. Of these groups, methyl, ethyl and phenyl are preferred.

$R^7$ is a monovalent hydrocarbon group of 1 to 10 carbon atoms, preferably 1 to 6 carbon atoms, examples of which include alkyl groups such as methyl, ethyl, propyl, isopropyl, butyl, isobutyl, tert-butyl, pentyl, neopentyl, hexyl and octyl, cycloalkyl such as cyclohexyl, alkenyl groups such as vinyl, allyl and propenyl, aryl groups such as phenyl, tolyl, xylyl and naphthyl, and aralkyl groups such as benzyl, phenylethyl and phenylpropyl. Of these groups, methyl and ethyl are preferred.

Specifically, formula (2) may be represented by the following formulae (6) to (10).

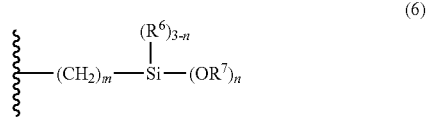

(6)

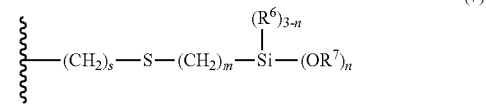

(7)

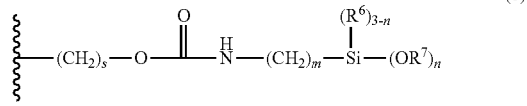

(8)

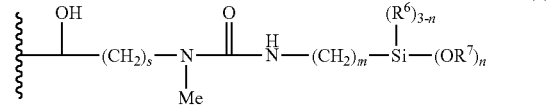

(9)

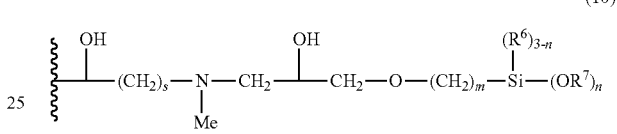

(10)

Herein m is an integer of 1 to 8, s is an integer of 1 to 8, $R^6$, $R^7$, n and the wavy line are as defined above, and Me is methyl.

Formula (3) may be represented by the following formulae (11) and (12).

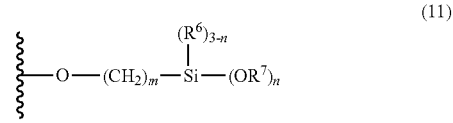

(11)

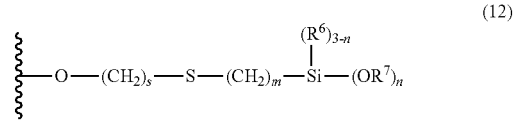

(12)

Herein $R^6$, $R^7$, m, n, s and the wavy line are as defined above.

Formula (4) may be represented by the following formulae (13) and (14).

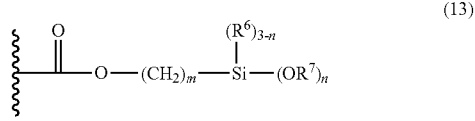

(13)

(14)

Herein $R^6$, $R^7$, m, n, s and the wavy line are as defined above.

Formula (5) may be represented by the following formula (15).

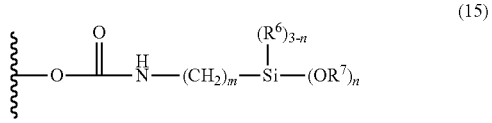

(15)

Herein $R^6$, $R^7$, m, n and the wavy line are as defined above.

The organosilicon compounds of the invention may be prepared by a plurality of methods. Those organosilicon compounds wherein formula (2) is represented by formula (6), wherein formula (3) is represented by formula (11), and wherein formula (3) is represented by formula (13) may be obtained by hydrosilylation reaction of a compound having a catechol group and a terminal alkenyl group with a hydrogenorganosilane compound in the presence of a catalyst.

Those organosilicon compounds wherein formula (2) is represented by formula (7), wherein formula (3) is represented by formula (12), and wherein formula (3) is represented by formula (14) may be obtained by thiol-ene reaction of a compound having a catechol group and a terminal alkenyl group with an organosilicon compound having a mercapto group.

The organosilicon compound wherein formula (2) is represented by formula (8) may be obtained by reaction of a compound having a catechol group and an aliphatic alcohol group with an organosilicon compound having an isocyanate group.

The organosilicon compound wherein formula (2) is represented by formula (9) may be obtained by reaction of a compound having a catechol group and a secondary amino group with an organosilicon compound having an isocyanate group.

The organosilicon compound wherein formula (2) is represented by formula (10) may be obtained by reaction of a compound having a catechol group and a secondary amino group with an organosilicon compound having an epoxy group.

The organosilicon compound wherein formula (5) is represented by formula (15) may be obtained by reaction of a compound having a catechol group and an aromatic alcohol group with an organosilicon compound having an isocyanate group.

Another embodiment is an adhesive composition comprising the organosilicon compound having a catechol group, represented by the general formula (1). Examples of the adhesive composition include a combination of the organosilicon compound with an inorganic material, a combination of the organosilicon compound with a low molecular weight material, a combination of the organosilicon compound with a high molecular weight material, and a combination of the organosilicon compound with a solvent, which may be used alone or in admixture. The organosilicon compound may be incorporated in any of the foregoing materials or solvents via reaction.

The content of the compound of formula (1) in the adhesive composition is not particularly limited. The content of the compound is preferably 0.001 to 50% by weight, more preferably 0.1 to 10% by weight. Too low contents of the compound may be less effective whereas too high contents may be uneconomical.

Preferably, the organosilicon compound of formula (1) is dissolved in a solvent prior to use. Suitable solvents include, but are not limited to, hydrocarbon solvents such as pentane, hexane, cyclohexane, heptane, isooctane, benzene, toluene and xylene, ether solvents such as diethyl ether, tetrahydrofuran and dioxane, ester solvents such as ethyl acetate and butyl acetate, aprotic polar solvents such as acetonitrile and N,N-dimethylformamide, protonic polar solvents such as methanol, ethanol alcohol and water, and halogenated hydrocarbon solvents such as dichloromethane and chloroform. Of these, protonic polar solvents are preferred because they can stabilize the catechol group. These solvents may be used alone or in admixture of two or more.

It is preferred for adhesion improvement and cost reduction that the organosilicon compound of formula (1) be dissolved in the solvent in a concentration of 0.001 to 50% by weight, specifically 0.1 to 10% by weight.

Acids or bases may be used as a pH control agent. Preferably the composition is at pH 2 to 13, more preferably pH 3 to 12.

The adhesive composition may further contain an inorganic material, for example, titanium oxide, silicon oxide, aluminum oxide, or zirconium oxide. The content of the inorganic material may be 0 to 80% by weight of the composition.

The adhesive composition may further contain a polymerizable monomer (low molecular weight material) in which the organosilicon compound is dissolvable and/or which is dissolvable in the solvent. The low molecular weight material typically has a molecular weight of up to 1,000, but is not particularly limited. When the material has a functional group, examples of the functional group include radically polymerizable groups such as hydroxyl, carbonyl, carboxyl, amino, thiol, cyano, sulfonyl, nitro, isocyanate, isothiocyanate, silyl, sulfide bond, amide bond, urea bond, ester bond, siloxane bond, vinyl and acrylic groups, cationic polymerizable groups such as cyclic ether and vinyl ether, and ring-opening metathesis polymerizable groups such as norbornenyl and dicyclopentadienyl. The number of functional groups is not particularly limited. The low molecular weight materials may be used alone or in admixture of two or more.

Specifically, suitable low molecular weight materials are hydrocarbons of 1 to 50 carbon atoms and may contain a linear, branched or cyclic structure or an aromatic group. Some or all hydrogen atoms of the hydrocarbon may be substituted. Suitable substituents include radically polymerizable groups such as a hydroxyl, carbonyl, carboxyl, amino, thiol, cyano, sulfonyl, nitro, isocyanate, isothiocyanate, alkylsilyl, alkoxysilyl, vinyl and acrylic groups, cationic polymerizable groups such as cyclic ether and vinyl ether, and ring-opening metathesis polymerizable groups such as norbornenyl and dicyclopentadienyl. The hydrocarbon may have one or more substituents. The hydrocarbon may contain a sulfide, amide, urea, ester or siloxane bond.

The content of the low molecular weight material is preferably up to 99%, more preferably up to 50%, and most preferably 1 to 30% by weight based on the adhesive composition.

Along with the solvent, the adhesive composition may further contain a polymer (high molecular weight material) which is dissolvable in the solvent. The high molecular weight material is typically a polymer having a weight average molecular weight of more than 1,000, preferably from more than 1,000 to 100,000, and more preferably 2,000 to 50,000, as measured by gel permeation chromatography (GPC) versus polystyrene standards, but is not particularly limited. When the material has a functional group, examples of the functional group include radically polymerizable groups such as hydroxyl, carbonyl, carboxyl, amino, thiol, cyano, sulfonyl, nitro, isocyanate, isothiocyanate, silyl, sulfide bond, amide bond, urea bond, ester bond, siloxane bond, vinyl and acrylic groups, cationic polymerizable groups such as cyclic ether and vinyl ether, and ring-opening metathesis polymerizable groups such as norbornenyl and dicyclopentadienyl. The number of functional groups is not particularly limited. High molecular weight materials obtained from reaction of such functional groups are also included. The high molecular weight materials may be used alone or in admixture of two or more.

Exemplary high molecular weight materials include natural high molecular weight materials such as proteins, nucleic acids, lipids, polysaccharides and natural rubbers; and synthetic high molecular weight materials such as phenolic resins, epoxy resins, melamine resins, urea resins, polyurethane, polyimide, polyamide-imide, polyethylene, polypropylene, polyvinyl chloride, polystyrene, polyvinyl acetate, acrylic resins, nitrile resins, isoprene resins, urethane resins, ethylene-propylene resins, epichlorohydrin resins, chloroprene resins, butadiene resins, styrene-butadiene resins, polyamide, polyacetal, polycarbonate, polyphenylene ether, polyethylene terephthalate, polybutylene terephthalate, cyclic polyolefin, polyphenylene sulfide, polytetrafluoroethylene, polysulfone, polyether sulfone, and polyether ether ketone, as well as copolymers and polymer alloys of two or more of the foregoing.

The content of the high molecular weight material is preferably up to 99%, more preferably up to 50%, and most preferably 1 to 30% by weight based on the adhesive composition.

As long as the objects of the invention are not impaired, the adhesive composition may further comprise additives such as surfactants, antiseptics, discoloration preventive agents, and antioxidants.

Substrates to be treated with the adhesive composition may be of any inorganic materials capable of reaction with a hydrolyzable silyl group to form a bond and any organic materials such as organic resins capable of interaction with a catechol group. The shape of the substrate is not particularly limited. Typical inorganic materials include inorganic fillers of silicon, titanium, zirconium, magnesium, aluminum, indium, tin and single or complex oxides thereof; glass fiber products such as glass fibers, glass cloth, glass tape, glass mat and glass paper; ceramics; and metal substrates such as iron, aluminum, copper, silver, gold and magnesium. Typical organic materials are epoxy resins, phenolic resins, polyimide resins, unsaturated polyester resins, heavy paper, wood, solid wood, and chipboard. The substrates are not limited to those listed herein.

The treatment method and curing conditions of the adhesive composition are not particularly limited. For example, the substrate may be directly treated with the adhesive composition by flow coating, dipping or spin coating. Alternatively, kneading treatment may be carried out by adding the adhesive composition to a base compound consisting of an untreated inorganic filler and a resin as a dispersing medium and mixing them. Typical curing procedure is heating and drying. Specifically, the substrate as surface treated is heated and dried at 60 to 180° C., preferably 80 to 150° C. for 5 minutes to 2 hours for thereby simultaneously accomplishing both solvent removal and chemical reaction between the silane coupling agent as the active ingredient in the surface treatment agent and the substrate surface.

EXAMPLE

Examples of the invention are given below by way of illustration and not by way of limitation. Me stands for methyl.

Synthesis of Organosilicon Compounds (16) to (18)

Synthesis Example 1

A 2-L separable flask equipped with a stirrer, reflux condenser, dropping funnel and thermometer was charged with 150 g (1 mole) of 4-allylcatechol and an amount ($1\times10^{-4}$ mole of platinum atoms) of a toluene solution of platinum-1,3-divinyl-1,1,3,3-tetramethyldisiloxane complex. To the flask kept at an internal temperature of 75-85° C., 122 g (1 mole) of trimethoxysilane was added dropwise over 2 hours. The contents were stirred at 80° C. for 1 hour, followed by cooling to room temperature. To the reaction mixture, 1,088 g of methanol was added. The resulting solution containing organosilicon compound (16) is designated silane solution A.

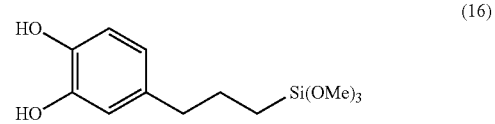

(16)

Synthesis Example 2

A 2-L separable flask equipped with a stirrer, reflux condenser, dropping funnel and thermometer was charged with 150 g (1 mole) of 4-allylcatechol and 3.5 g of 2,2'-azobis(2-methylbutyronitrile) available as V-59 from Wako Pure Chemical Industries, Ltd. To the flask kept at an internal temperature of 75-85° C., 196 g (1 mole) of 3-mercaptopropyltriethoxysilane was added dropwise over 1 hour. The contents were stirred at 80° C. for 1 hour, followed by cooling to room temperature. To the reaction mixture, 1,384 g of methanol was added. The resulting solution containing organosilicon compound (17) is designated silane solution B.

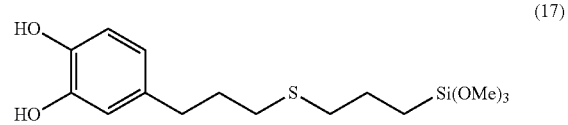

(17)

Synthesis Example 3

A 2-L separable flask equipped with a stirrer, reflux condenser, dropping funnel and thermometer was charged with 126 g (1 mole) of pyrogallol, 0.25 g of dioctyltin oxide, and 662 g of MIBK. To the flask kept at an internal temperature of 90° C., 205 g (1 mole) of 3-isocyanatopropyltriethoxysilane was added dropwise over 1 hour. The contents were stirred at 90° C. for 1 hour, followed by cooling to room temperature. To the reaction mixture, 662 g of methanol was added. The resulting solution containing organosilicon compound (18) is designated silane solution C.

(18)

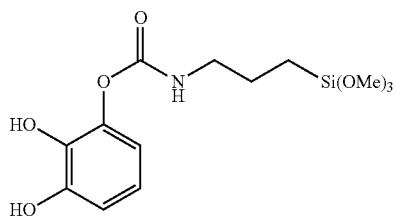

[Test of Adhesion Between Glass Fiber and Epoxy Resin]

Examples 1 to 3 and Comparative Examples 1 and 2

The silane solutions A to C obtained above and a 1 wt % dilution of 3-aminopropyltriethoxysilane (KBE-903, Shin-Etsu Chemical Co., Ltd.) in water and methanol were used as surface treatment agent. Each surface treatment agent was applied to glass fibers having a diameter of 20 μm and dried at 100° C. for 30 minutes, yielding surface treated glass fibers. To the surface treated glass fibers, a thermosetting composition composed of an epoxy resin (JER828, Japan Epoxy Resins Co., Ltd.) and triethylenetetramine as curing agent was applied in the form of droplets having a diameter of several tens to several hundreds of microns (μm) such that droplets were kept apart. The droplets were heat cured at 80° C. for 1.5 hours and post-cured at 100° C. for 2 hours, yielding spherical resin beads. The shear strength between the surface treated glass fiber and the epoxy resin was measured by the microdroplet test using evaluation equipment for interfacial property of composite materials (HM410, Tohei Sangyo Co., Ltd.). The shear strength per unit area (τ, MPa) is determined according to the equation of τ=F/πDL wherein D is the fiber diameter (μm), L is the length (μm) of the fiber portion embedded in the spherical resin bead, and F is the load (mN) required to pull the spherical resin bead out of the fiber in fiber axial direction. The active ingredient of the surface treatment agent is shown in Table 1 together with the results of shear strength.

TABLE 1

|  | Active ingredient of surface treatment agent | Shear strength (MPa) |
| --- | --- | --- |
| Example 1 | Silane solution A | 42.1 |
| Example 2 | Silane solution B | 42.2 |
| Example 3 | Silane solution C | 43.6 |
| Comparative Example 1 | KBE-903 | 40.7 |
| Comparative Example 2 | Untreated | 33.7 |

The results of Examples and Comparative Examples demonstrate that the substrate surface modified with the adhesive composition is tightly adherent to an epoxy resin.

Japanese Patent Application No. 2014-061196 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound of formula (1):

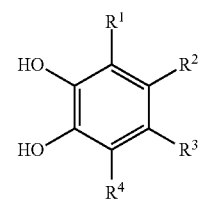

wherein $R^1$ to $R^4$ are each independently selected from the group consisting of hydrogen, substituted or unsubstituted monovalent hydrocarbon groups which may be separated by at least one bond selected from ether, thioether, carbonyl, and thiocarbonyl bonds, and organic groups of formulae (3) to (5), and at least one of $R^1$ to $R^4$ is any one of organic groups of formulae (3) to (5):

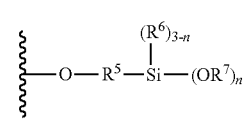

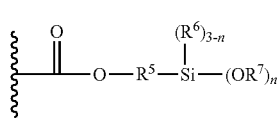

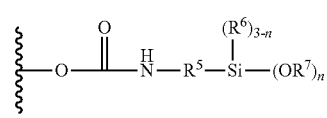

wherein $R^5$ is a substituted or unsubstituted divalent hydrocarbon group which may be separated by at least one bond selected from ether, thioether, carbonyl, thiocarbonyl, amino, urethane, and urea bonds, $R^6$ is an alkyl group of 1 to 10 carbon atoms or aryl group of 6 to 10 carbon atoms, $R^7$ is an alkyl group of 1 to 20 carbon atoms, alkenyl group of 2 to 10 carbon atoms, aryl group of 6 to 10 carbon atoms or acyl group of 1 to 20 carbon atoms, n is an integer of 1 to 3, and the wavy line designates a bonding site to the benzene ring.

2. The organosilicon compound of claim 1 wherein formula (3) is formula (11) or (12):

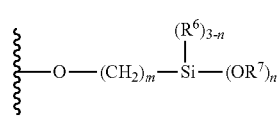

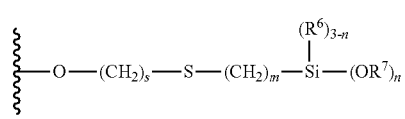

wherein m is an integer of 1 to 8, s is an integer of 1 to 8, and $R^6$, $R^7$, n and the wavy line are as defined above, formula (4) is formula (13) or (14):

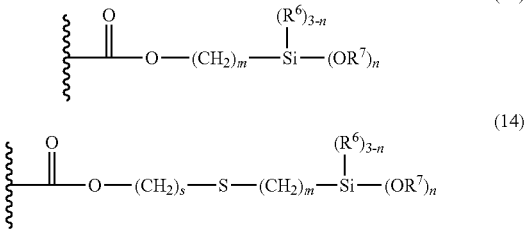

wherein m is an integer of 1 to 8, s is an integer of 1 to 8, and $R^6$, $R^7$, n and the wavy line are as defined above, formula (5) is formula (15):

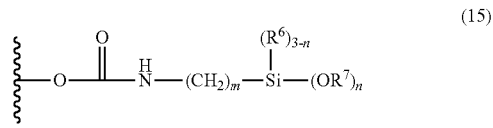

wherein m is an integer of 1 to 8 and $R^6$, $R^7$, n and the wavy line are as defined above.

3. An adhesive composition comprising the organosilicon compound of claim 1.

4. An article comprising a substrate having a surface treated with the adhesive composition of claim 3.

5. The article of claim 4 wherein the substrate is a glass fiber product selected from the group consisting of glass cloth, glass tape, glass mat, and glass paper.

6. The article of claim 4 wherein the substrate is an inorganic filler.

7. The article of claim 4 wherein the substrate is a ceramic or metal.

8. The organosilicon compound of claim 1, wherein $R^1$ to $R^4$ are each independently selected from the group consisting of hydrogen, substituted or unsubstituted monovalent hydrocarbon groups which may be separated by at least one bond selected from ether, thioether, carbonyl, and thiocarbonyl bonds, and the organic group of formula (5), and at least one of $R^1$ to $R^4$ is the organic group of formula (5).

* * * * *